United States Patent [19]

Webster

[11] Patent Number: 4,538,908

[45] Date of Patent: Sep. 3, 1985

[54] PARTICULATE SAMPLE ANALYZING INSTRUMENT EMPLOYING VIBRATION TO COMPACT THE SAMPLE

[75] Inventor: Donald R. Webster, Laurel, Md.

[73] Assignee: Pacific Scientific Company, Anaheim, Calif.

[21] Appl. No.: 422,275

[22] Filed: Sep. 23, 1982

Related U.S. Application Data

[63] Continuation-in-part of Ser. No. 236,580, Feb. 29, 1981, Pat. No. 4,422,760.

[51] Int. Cl.³ .......................... G01J 3/48; G01N 1/10
[52] U.S. Cl. ..................................... 356/36; 356/418; 250/576
[58] Field of Search ................. 356/36, 244, 418, 445, 356/426, 246; 250/573, 574, 576; 73/863

[56] References Cited

U.S. PATENT DOCUMENTS

| | | | |
|---|---|---|---|
| 2,371,192 | 3/1945 | Short | 250/574 X |
| 2,844,067 | 7/1958 | Borg | 356/36 |
| 3,549,263 | 12/1970 | Osawa et al. | 356/445 |
| 4,040,747 | 8/1977 | Webster | 356/244 X |

FOREIGN PATENT DOCUMENTS

| | | | |
|---|---|---|---|
| 171134 | 5/1966 | U.S.S.R. | |
| 0179504 | 7/1969 | U.S.S.R. | 356/36 |

Primary Examiner—Vincent P. McGraw
Assistant Examiner—S. A. Turner
Attorney, Agent, or Firm—Lane, Aitken & Kananen

[57] ABSTRACT

In an instrument for optically analyzing particulate samples such as grain samples, the sample is introduced into a chute which is received in a vibrating apparatus to vibrate the grain in the chute and compact it. The chute is then dropped to a carriage which transports the chute and the grain through a beam of narrow band infrared light. A photocell is positioned to detect the amount of light passing through the grain sample.

12 Claims, 5 Drawing Figures

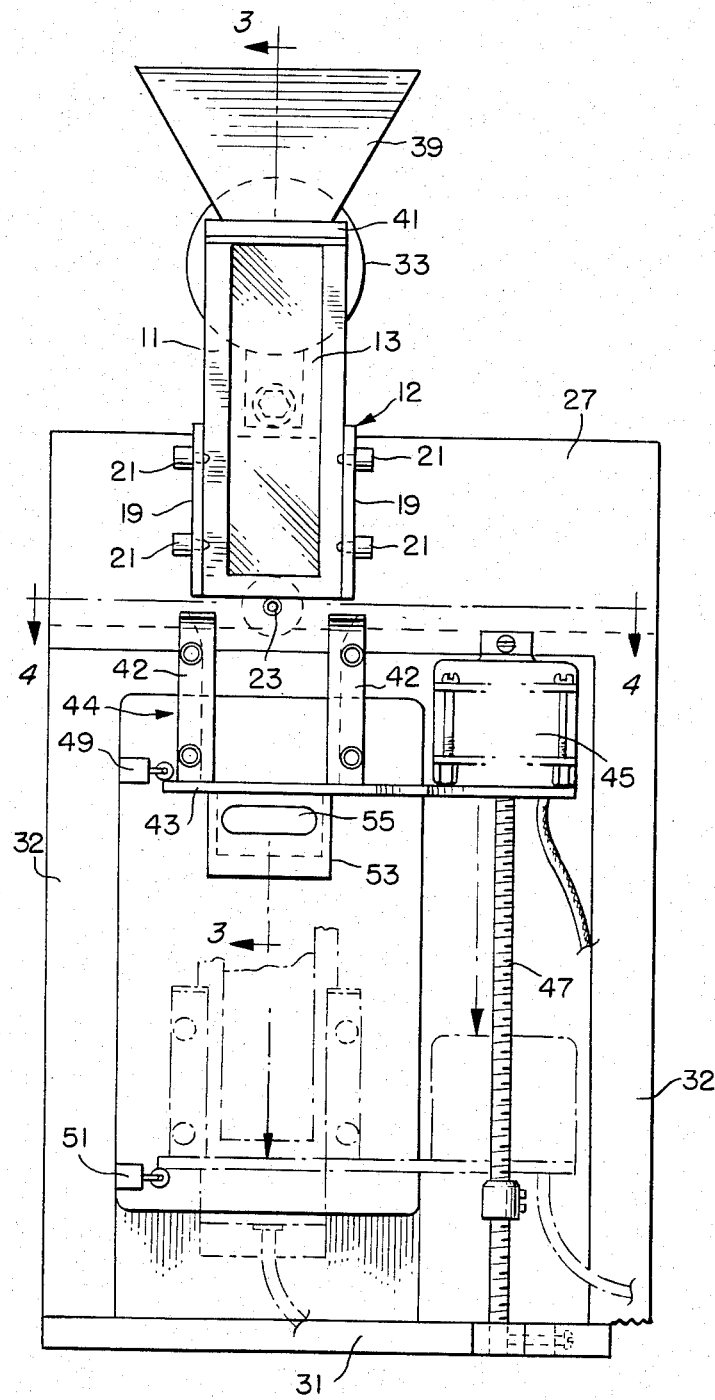
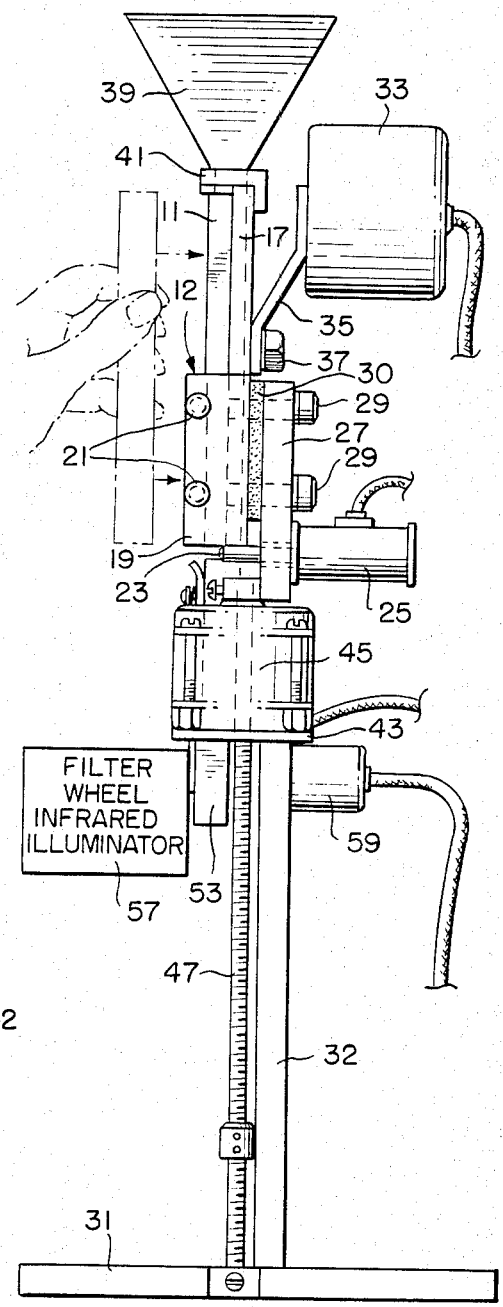

PARTICULATE SAMPLE ANALYZING INSTRUMENT EMPLOYING VIBRATION TO COMPACT THE SAMPLE

CROSS REFERENCE TO RELATED APPLICATIONS

This application is a continuation-in-part of U.S. application Ser. No. 236,580 filed Feb. 29, 1981, invented by the inventor of this application, now U.S. Pat. No. 4,422,760.

BACKGROUND OF THE INVENTION

This invention relates to an instrument and method for optically analzing particulate samples, and, more particularly, to an instrument in which vibration is used to compact the particulate samples and eliminate any cavities or voids therein.

In U.S. Pat. No. 4,040,747 to Donald R. Webster, issued Aug. 9, 1977, there is disclosed a relatively low cost instrument for measuring and analyzing the optical properties of organic materials to determine the percentages of certain constituents of the test materials. This instrument was developed to satisfy a need for a low cost instrument to rapidly determine the moisture, oil and protein content in produce and grain products. In the instrument disclosed in the patent, a source of wide-band infrared light is positioned to illuminate a sample of ground grain through a filter assembly in which interference filters are arranged in a wheel configuration mounted for rotation about an axis. As the filter wheel rotates, each filter is brought successively into the infrared light beam. As each filter is moved through the light beam by the filter wheel, the angle of incidence of the light beam on the filter changes and this changes the wavelength transmitted through the filter. Moreover, each filter provides a different range of wavelengths. By detecting the amount of reflection from the sample at selected specific wavelengths and the relationships of these reflectance values, the oil, protein, and water content of the sample can be accurately and quickly determined.

U.S. application Ser. No. 45,089, filed June 4, 1979 discloses an instrument similar to that disclosed in the Webster U.S. Pat. No. 4,040,747, but in which the grinding of the grain is carried out automatically in the instrument at the time the measurement is made. When the instrument is started, the grain introduced into a hopper at the top of the instrument is ground and directed into a chute, the bottom of which is arranged to receive infrared light passing through the filter wheel. The bottom of the chute is enclosed by an impeller which removes grain from the chute. As the impeller moves the grain from the chute, the grain in the chute moves through the infrared beam received by the filter wheel to provide an automatic averaging from the sample being analyzed.

The instrument disclosed in application Ser. No. 236,580 is similar to that in U.S. Ser. No. 45,089, but in which the impeller at the bottom of the chute is replaced by a vibrating trough positioned at the bottom of the chute. The vibrating trough acts as a conveyor to move the analyzed grain away from the chute. When the vibrator is off, the trough serves as a gate to stop the flow of grain. The vibrating trough also serves as an agitator by sending vibrations through the grain in the trough and up through the column of the grain positioned in the chute thereby preventing any clogging of the grain in the chute.

In the instruments as described in the above identified patent and pending applications, the grain sample is preferably ground in order to give the most precise measurement of the constituents of the grain sample. In some applications in which such precision is not necessary, it has been proposed to optically analyze the grain without grinding. When the grain is not ground, the best way to optically analyze the grain is to measure the transmittance of the grain instead of the reflectance. As in the instruments of the above mentioned patent and applications, the grain sample is irradiated with narrow band infrared light by means of a filter wheel. A photodetector is positioned to receive the light transmitted to the sample. From the light transmitted through the sample as detected by the photocell, a determination can be made as to the constituents of the grain sample.

SUMMARY OF THE INVENTION

In the instruments described above, it is important for the sample to be properly compacted so that there are no voids or cavities in the sample. In accordance with the present invention, a simple method and instrument are provided in which the optical measurements on grain samples can be quickly made without danger of any cavities occurring in the sample. The grain sample, after being introduced into a container, is vibrated to compact the sample and the optical measurements on the sample are made after the grain has been compacted by vibrations. This method of compacting the grain inherently occurs in the copending application Ser. No. 236,580. In the instrument of the invention, the sample container is in the form of a chute. A vibrating apparatus is provided to receive the chute and vibrate the chute after grain has been introduced into the chute. Following vibration, the chute is dropped into a transport mechanism which moves the chute and the compacted bed of grain contained in the chute through an infrared beam of light directed onto the sample by a filter wheel apparatus. In the specific embodiment disclosed in the application, a photodetector is provided for detecting the light transmitted through the sample as it is moved through the infrared beam. Alternatively, the photodetector could detect the light reflected from the sample. From the photodetector signal, an accurate determination of the constituents in the grain sample can be determined. In this manner, a very simple and convenient instrument and method is provided for making optical measurements on grain samples without danger of voids or cavities occurring in the sample.

BRIEF DESCRIPTION OF THE DRAWINGS

FIG. 1 is a front view in elevation of the system of the present invention;

FIG. 2 is a side view in elevation illustrating the instrument of the present invention;

DESCRIPTION OF A SPECIFIC EMBODIMENT

Figure 3:
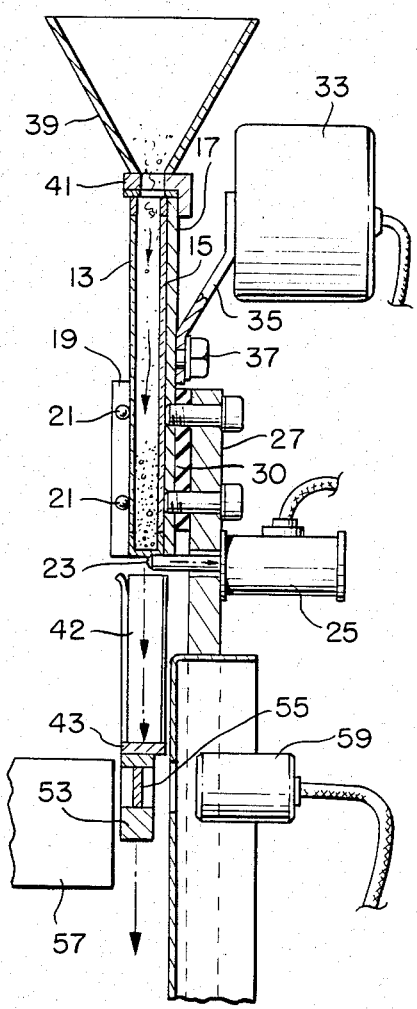
FIG. 3 is a sectional view in elevation taken along the line 3—3 of FIG. 1.
Figure 4:
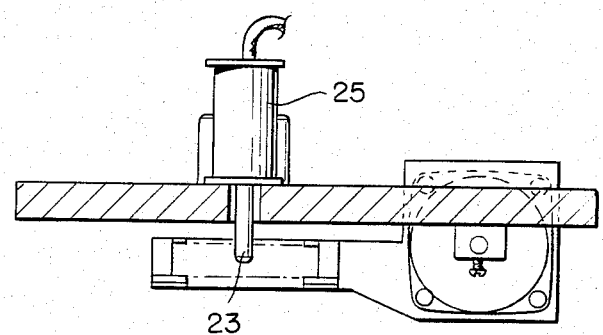
FIG. 4 is a sectional plan view of the instrument of the present invention taken along the line 4—4.

In the specific embodiment of the invention shown in FIGS. 1-4 and described below, the instrument makes transmittance measurements on grain samples. The invention, however, is equally applicable to instruments which are designed to make reflectance measurements on the grain samples.

As shown in FIGS. 1-4, the instrument employs a chute 11 for receiving the grain sample to be analyzed. The chute 11 has a rectangular cross-section as viewed in FIG. 4 and has front and back sidewalls 13 and 15, which are transparent to infrared light. In an instrument designed for reflectance measurement, only one of the walls 13 or 15 would be transparent. The chute 11, which has an open top and a closed bottom, is designed to be received in a holder 12 of a vibrating apparatus. The holder 12 comprises a back wall 17 having a vertical dimension the same length as the chute 11 and sidewalls 19. In operation, the chute is placed between the sidewalls 19 against the back wall 17 and is retained in the holder 12 by spring loaded bullet detents 21 mounted in the sidewalls 19. The bottom of the chute 11, when received by the holder 12, will rest upon a pin 23 connected to the armature of a solenoid 25. When the solenoid 25 is energized, the pin 23 will be withdrawn and will allow the chute 11 to fall vertically out of the holder 12. The back wall 17 is secured to a cross member 27 by means of screws 29 threaded into the back wall 17. A resilient cushion 30 is provided between the back wall 17 and the cross member 27. The cross member 27 is supported by legs 32 mounted on a base 31 to position the chute holder 12 elevated above the base 31. An electrical vibrator 33 having a mounting arm 35 is mounted on the back wall 17. The vibrator 33 is mounted by securing the mounting arm 35 to the back wall 17 by means of a screw 37 threaded into the back wall 17. The mounting arm 35 extends diagonally and upwardly away from the back walls 17 to support the vibrator 33 in a cantilevered position from the back wall 17.

A funnel 39 is fixed to the top of the back wall 17 by means of a bracket 41 and is positioned so that when the chute 11 is received in the chute holder 12, the bottom opening of the funnel 39 will be aligned with the open top end of the chute 11. When the pin 23 is retracted, the chute 11 will fall from the upper chute holder 12 into a lower chute holder 44 comprising side walls 42, which define slots to receive the side edges of the chute 11, and a bottom platform 43. When the pin 23 is retracted, the chute falls into the slots defined by the sidewalls 42 and rests against the platform 43. The platform 43 is fixed to a reversible motor 45, which is adapted to travel up and down a fixed screw 47 extending vertically between the base 31 and the cross member 27. The screw 47 extends axially through the center of the motor and a worm gear, not shown, driven by the armature of the motor 45 turns on the screw 47. Accordingly, when the motor 45 is energized to drive its armature in one direction, the motor 43 will move down the screw 47 and when the motor is energized to turn its armature in the opposite direction, the motor will move up the screw 47.

A limit switch 49 is positioned to be actuated by the platform 43 when the platform 43 and the motor 45 are in the upper extreme position as shown in solid lines in FIG. 1 and a limit switch 51 is positioned to be actuated by the platform 43 when the platform 43 of the motor 45 are in the lower extreme position shown in phantom in FIG. 1. Mounted on the platform 43 and hanging below the platform is a standard sample holder 53 defining an aperture in which is mounted a standard transmittance sample 55. A filter wheel infrared illuminator 57 is positioned to transmit a beam of infrared light toward a photodetector 59. When the motor 45 and the platform 43 are in the upper extreme position, as shown in full lines in FIGS. 1 and 2, the standard sample 55 will be positioned in the infrared beam between the illuminator 57 and the photodetector 59. The filter wheel illuminator may be a paddlewheel filter assembly, such as that disclosed in U.S. Pat. No. 4,040,747 or it may be a drum filter wheel assembly as shown in the Johnson U.S. Pat. No. 4,082,464. As disclosed in these two patents, the filter wheel illuminator transmits a narrow bandwidth infrared component from an infrared source and continuously scans the transmitted wavelength through a plurality of ranges of wavelengths.

In operation, the operator of the instrument will insert the chute 11 into the upper holder 12 through the bullet detents 21 and then fill the chute with grain through the funnel 39. The instrument will then be started by a start button (not shown in FIGS. 1-4) whereupon the vibrator 33 will begin vibrating the chute holder 12 and compact the grain in the chute 11 into a bed having no cavities or voids. The resilient cushion 30 enables good vibrating motion to be applied to the chute holder without stressing the supporting legs 32. At the same time the vibrator 33 is energized, the filter wheel illuminator 57 will be turned on and begin directing an infrared beam through the standard transmittance sample 55 to the photodetector 59 while scanning the narrow wavelength band transmitted through the selected ranges of wavelengths. While the standard sample is irradiated by the infrared beam, the resulting output signal of the photodetector is sampled at selected wavelengths of the infrared beam and stored in a computer (not shown). After a time delay sufficient for the filter wheel and the illuminator to scan the transmitted wavelength through the entire wavelength range, the vibrator 33 will be de-energized and the solenoid 25 will be energized to retract the pin 23. Thereupon the chute 11 will fall from the chute holder 12 into the chute holder 44 and the motor 45 will be energized to begin carrying the platform 43 and the chute 11 downwardly through the infrared beam passing between the illuminator 57 and the photodetector 59. As the grain sample is moved through the infrared beam in this manner, output signals from the photodetector are sampled at selected wavelengths of the infrared beam and applied to the computer. The computer then from the signals received from the photodetector, including those received in response to the beam transmitted through the standard transmissivity sample as well as through the grain sample, computes the percentage of oil, protein and water in the grain sample. The mathematics used by the computer for determining the constituents from reflectance measurements is discussed in U.S. Pat. No. 4,040,747. The same equations with different constants are used to determine the constituents from transmittance measurements.

As described above, the photocell 59 is positioned to receive the infrared beam transmitted through the grain sample to make transmittance measurements on the sample. In a refelectance measuring instrument, the plurality of photocells would be positioned in the same side of the sample as the illuminator to receive light reflected from the sample.

The motor 45 will carry the chute 11 downwardly while measurements are made by the photodetector 59 until the platform 43 actuates the limit switch 51, whereupon the energization to the motor 45 will be reversed and it will carry the platform 43 back up to its upper position until the limit switch 49 is actuated whereupon the motor will be de-energized. The chute 11 may then be removed from the apparatus to empty the grain sample contained by the chute 11 so that it may again be replaced into the upper chute holder 12 to receive another grain sample through the funnel 39.

Figure 5:
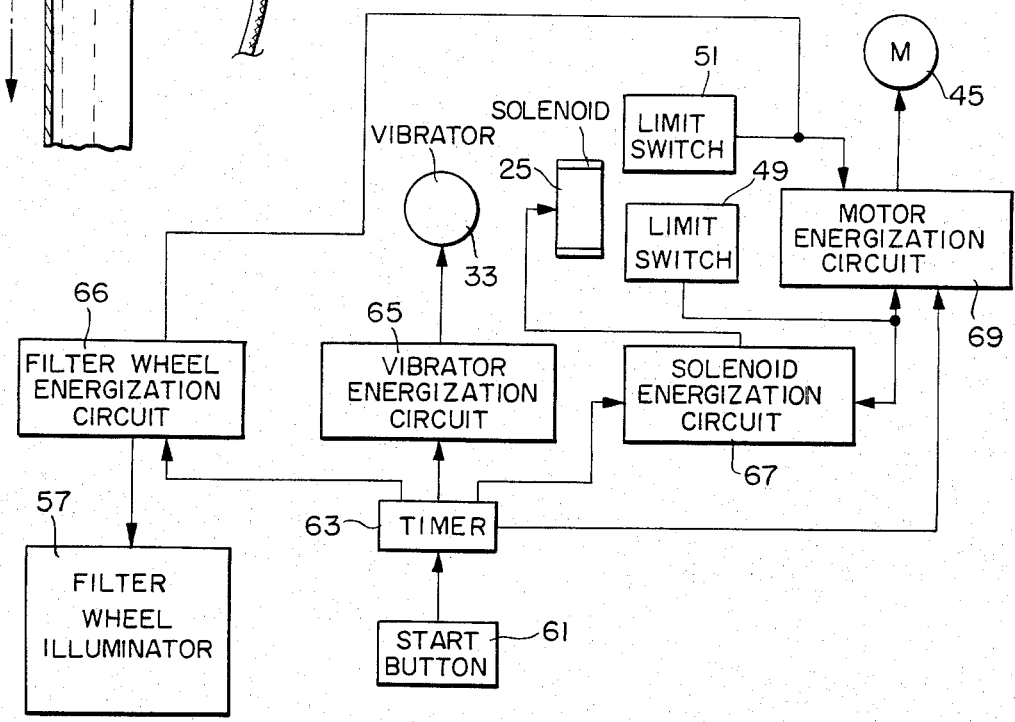
FIG. 5 is a block diagram of the circuit for effecting automatic operation of the instrument shown in FIGS. 1-4.

FIG. 5 is a block diagram illustrating the circuit for effecting automatic operation of the instrument shown in FIGS. 1-4. After the sample holder has been placed in the holder 12 and filled with grain, operation of the instrument is initiated by actuating a start button 61 which starts a timer 63. The timer 63, upon being started, applies an enabling signal to a vibrator energization circuit 65, which then energizes the vibrator 33. The vibrator 33 will then vibrate the chute 11 containing the grain sample in the holder 12. The timer 63, upon being started by the start button 61, also applies an enabling signal to filter wheel energization circuit 66, which energizes the filter wheel illuminator 57 to cause it to start turning the filter wheel assembly and generate the infrared light beam directed toward the photocell 59. After a time delay, the timer 63 will cease applying the enabling signal to the energizing circuit 65 whereupon the vibrator 33 will be de-energized. At the same time, the timer 63 will apply an enabling signal to a solenoid energization circuit 67, which, upon receiving the signal from the timer 63, energizes the solenoid 25. Upon being energized, the solenoid 25 retracts the pin 33 to cause the chute 11 to fall into the lower chute holder 44. A short time after applying the enabling signal to the solenoid energization circuit 67, the timer 63 applies an enabling signal to a motor energization 69, which, in response to receiving the enabling signal from the timer 63, energizes the motor 45 in a direction to move down the screw 47. Accordingly, after the chute 11 has fallen into the holder 44, the motor 45 begins to move the platform 43 with the chute 11 downwardly. When the platform reaches its lower limit, as shown in phantom in FIG. 1, the limit switch 51 is actuated and applies a signal to the motor energization circuit 69 to cause it to reverse the energization of the motor. The signal from the limit switch 51 is also applied to the filter wheel energization circuit 66 to cause it to de-energize the filter wheel illuminator. The motor 45, upon being energized in a reverse direction, moves the platform back up to the upper position until it reaches the limit switch 49, which, upon being actuated, applies a signal to the motor energization circuit 69 causing it do de-energize the motor 45 in the upper position. In addition, the limit switch 49 applies a signal to the solenoid energization circuit 67 to cause it to de-energize the solenoid 25. In this manner, the control system illustrated in FIG. 5 effects automatic operation of the instrument to first vibrate the grain sample, then drop the chute containing the grain sample into the lower holder 44, then carry the chute with the grain sample through the infrared beam, and then move the carriage and the sample holder back to the upper position after the measurements have been made.

As explained above, while the above described specific embodiment of the instrument responds to the transmittance of the grain sample by detecting the amount of infrared light transmitted through the grain sample, the invention is equally applicable to an instrument in which the amount of infrared light is reflected from the grain sample. As used in this application, light reflected from the sample or transmitted through the sample is referred to as light making optical contact with the sample.

The above described instrument and method are designed particularly for analyzing grain samples. However, it will be appreciated that the method and apparatus are applicable to optically analyzing other samples in particulate form which would benefit from being compacted by vibration. Also, in the preferred embodiment of the invention, the sample chute after being vibrated in the vibrating apparatus is automatically transported to the mechanism for carrying this sample through the infrared beam. The invention in its broadest form is applicable to having separate vibrating apparatus to compact the grain and carriage apparatus to transport the chute through the infrared beam wherein the chute would be moved by hand from the vibrating apparatus to the carriage apparatus. These and many other modifications may be made to the above described specific embodiment of the invention without departing from the spirit and scope of the invention which is defined in the appended claims.

I claim:

1. A method of analyzing a particulate sample comprising introducing the sample into a container, vibrating the sample within said container to compact the particulate sample during a first interval, then during a second interval after said first interval, directing a beam of light onto the sample compacted in said container while said sample is not being vibrated, detecting the intensity of the light from said beam after the light has come in optical contact with said sample.

2. A method as recited in claim 1, wherein said sample comprises grain and said beam of light is infrared light.

3. A method as recited in claim 1, wherein the step of vibrating the particulate sample is carried out by vibrating the container into which the particulate sample is introduced.

4. A method as recited in claim 1, further comprising moving said sample contained in said container through said beam of light while the step of detecting the intensity of the light is being carried out.

5. A method as recited in claim 1, wherein the step of vibrating said sample is performed at a first staion and the step of directing a beam of light onto the sample is performed at a second station, said method including the step of transporting said container from said first station to said second station between the step of vibrating the sample and the step of directing a beam of light onto the sample.

6. An optical instrument for analyzing particulate sample material comprising a chute having walls defining an enclosure adapted to receive a particulate sample, at least a portion of one of said walls being transparent, means to vibrate said chute including all of said walls of said enclosure to compact the particulate sample within said chute against the transparent portion of said wall, means to irradiate said sample compacted in said chute with a beam of light through the transparent portion of said wall and a photodetector positioned to receive light from said beam after the light has come into optical contact with the sample compacted in said chute.

7. An instrument as recited in claim 6, wherein said means to vibrate said sample comprises a holder to receive said chute and an electric vibrator connected to said holder to vibrate said holder and the chute when received by said holder.

8. An optical instrument as recited in claim 6, wherein said beam of light comprises an infrared beam of light.

9. A method of analyzing a particulate sample comprising introducing the sample into a container having a plurality of walls defining an enclosure, at least a portion of one of said walls being transparent, vibrating said container including all of said walls to compact the particulate sample against the transparent portion of said wall, directing a beam of light through the transparent portion of said wall onto the sample compacted against the transparent portion of said wall, and detecting the intensity of the light from said beam after the light has come into optical contact with said sample.

10. A method, as recited in claim 9, comprising moving said container through said beam of light while the step of detecting the intensity of light is being carried out.

11. An optical instrument for analyzing particulate sample material comprising a chute adapted to receive a particulate sample, means to vibrate said sample within said chute to compact the particular sample within said chute, a source of light, said chute having a wall transparent to light from source, said source of light comprising means to irradiate said sample through said transparent wall, carriage means to support said chute with said beam of light irradiating said sample through said transparent wall and to move said chute with said sample through said beam of light, and a photodetector positioned to receive light from said beam after the light has come into optical contact with the sample compacted in said chute.

12. An optical instrument as recited in claim 11, further comprising means to automatically move said chute from said means to vibrate said sample into said carriage means after the completion of the vibration of said sample by said vibration means.

* * * * *